United States Patent [19]

Komen et al.

[11] Patent Number: 5,066,436
[45] Date of Patent: Nov. 19, 1991

[54] PROCESS FOR MICROENCAPSULATION

[75] Inventors: Joseph Komen, Eb Haarlem; Jan W. Groenendaal, EE Delft, both of Netherlands

[73] Assignee: Gist-Brocades N.V., Delft, Netherlands

[21] Appl. No.: 457,257

[22] Filed: Dec. 27, 1989

[30] Foreign Application Priority Data

Jan. 4, 1989 [EP] European Pat. Off. ........ 89200015.9

[51] Int. Cl.$^5$ .............................................. B01T 13/02
[52] U.S. Cl. ................. 264/4.3; 428/402.21; 428/402.22; 424/462; 424/457; 427/213.32; 514/963
[58] Field of Search ..................... 264/4.3; 428/402.21, 428/402.22; 424/462, 497; 514/963; 427/213.32

[56] References Cited

U.S. PATENT DOCUMENTS

| | | | |
|---|---|---|---|
| 3,691,271 | 9/1972 | Charle et al. | 424/28 |
| 3,956,172 | 5/1976 | Saeki et al. | 252/316 |
| 4,272,398 | 6/1981 | Jaffe | 252/316 |
| 4,294,921 | 10/1981 | Yamaguchi et al. | 430/621 |
| 4,601,863 | 7/1986 | Shio et al. | 264/4.3 |
| 4,722,838 | 2/1988 | Tocker | 424/81 |
| 4,976,961 | 12/1990 | Norbury et al. | 424/401 |

Primary Examiner—Robert L. Stoll
Assistant Examiner—Nina Bhat
Attorney, Agent, or Firm—Emmanuel J. Lobato; Robert E. Burns

[57] ABSTRACT

A process for microencapsulating bioactive substances in biocompatible polymers according to the phase-separation principle, wherein an excess of an ethyl or isopropyl ester of a straight-chain fatty acid having 12-18 carbon atoms is used as the hardening liquid, and the pharmaceutical compositions containing the microcapsules prepared by this process. Isopropyl myristate and isopropyl palmitate are preferred hardening liquids.

19 Claims, 4 Drawing Sheets

PROCESS FOR MICROENCAPSULATION

This invention relates to a process for microencapsulating bioactive substances in biocompatible polymers according to the phase-separation principle and to pharmaceutical compositions containing the microcapsules prepared by this process.

Microencapsulation of bioactive substances in biocompatible polymers is useful for the production of controlled-release preparations. The polymer used thereby determines the release characteristics of the bioactive substances. Biocompatible polymers which are also biodegradable are especially suitable for the production of injectable preparations.

Technologies of microencapsulation have been described by W. Fong in "Controlled Release Systems: Fabrication Technology" Vol. I Editor Dean Hsieh 1989, CRD Press, Florida, 1988, chapter 5, page 81-108 "Microencapsulation by solvent evaporation and organic phase-separation processes". There it is disclosed, that the principle of phase-separation, as opposed to solvent-dispersion, is especially suitable for encapsulating hydrophilic bioactive substances, but that it is also applicable to water-insoluble ones. The products of encapsulation may be true, "heterogeneous", microcapsules wherein the polymer encapsulates the bioactive core. The products may also be "homogeneous microspheres", wherein the bioactive substance is dispersed in the polymer.

Microencapsulation by phase-separation of hydrophilic bioactive substances in biodegradable polymers has been disclosed in EP 0052510 and in GB 2165517. Microencapsulation of a hydrophilic bioactive substance in non-biodegradable polymers has been disclosed by S. Benita et al. J. Pharm. Pharmacol. 1985, 391-395, "Microencapsulation of Paracetamol Using Polyacrylate Resins (Eudragit Retard)". These techniques generally comprise the following steps:

a. Dispersing a bioactive substance in a solution (in an organic solvent which is not miscible with water) of a biocompatible polymer;

b. Adding to the dispersion a so-called non-solvent (or coacervation agent), an organic liquid which is not miscible with the biocompatible polymer. This results in coacervation (or phase-separation), whereby the biocompatible polymer is deposited on the dispersed bioactive substance to form "embryonal" microcapsules;

c. Extracting the residual organic solvent out of the "embryonal" microcapsules and hardening them by adding to the dispersion an excess, with respect to the combined volume of solvent and non-solvent, of a so-called hardening liquid;

d. Collecting the hardened microcapsules from the dispersion, washing the microcapsules, and drying the microcapsules by any of the methods generally known in the art.

Hydrophilic bioactive substances which may be encapsulated by such processes are polypeptides such as luteinizing hormone, somatostatin and interferon. They are mostly dispersed in water before dispersing them in the organic solvent, but this is not always necessary (see e.g. GB 2165517). Lipophilic bioactive compounds such as steroids can also be encapsulated.

Biocompatible, biodegradable polymers which are known to be useful in encapsulating bioactive substances in such processes are polylactides, polyglycolides and copolymers of lactides and glycolides. Useful non-biodegradable biocompatible polymers are the pH-dependent polyacrylate resins such as EUDRAGIT-S and the pH-independent polyacrylate resins such as EUDRAGIT-RS and ethylcellulose.

Organic solvents which are miscible with the polymer and with the non-solvent while being immiscible with water are halogenated hydrocarbons, such as dichloromethane ($CH_2Cl_2$).

Useful non-solvents are silicone oils.

The invention concerns in particular the step of hardening the microcapsules. The hardening liquid to be used in this step has to extract efficiently and fully any solvent and non-solvent from the microcapsules without dissolving the biodegradable polymer or the bioactive substance and without misforming the microcapsules or causing their aggregation. While the amount of any residues in the microcapsules has to be kept at a minimum, any residual amount of hardener has to be absolutely biocompatible.

Up to now only a very limited number of liquids has actually been used as hardening liquid.

EP 0052510 discloses as hardening liquids alkane organic solvents such as heptane. GB 2165517 points out that these compounds tend to leave a substantial amount of residue in the ready capsules, and that they are inflammable and/or toxic. Therefore GB 2165517 is directed to the use as hardening liquids of fluor- or fluorhalogen hydrocarbons, such as those known under the general name Freon ®, which are stated to leave a smaller amount of residue and to be less toxic. However, the amount of residue is actually still substantial and these compounds are not in general use for systemic medical applications other than inhalation and they have not been cleared and declared free of toxicity. Also, while GB 2165517 recommends the application of these compounds in the preparation of microcapsules based on a variety of biocompatible, biodegradable polymers, for example those of L-lactide, DL-lactide and the copolymers of DL-lactide and glycolide, only the latter, in a 2% solution, was actually used in the six examples of GB 2165517. Extensive attempts to prepare microcapsules according to GB 2165517 using both Freon 113 ® (1,1,2 trichlorotrifluoroethane) and Freon 11 ® (trichlorofluoro-methane) as the hardening liquids and DL-lactide as the biocompatible polymer in both 2% and 10% w/w solution, have all ended in failure of the microcapsules to harden.

It has now been found that ethyl and isopropyl esters of straight-chain fatty acids having 12-18 carbon atoms are outstandingly effective as hardening liquids for use in preparing microcapsules according to the phase-separation principle. Examples of such compounds are ethyl stearate, isopropyl stearate, ethyl oleate and preferably isopropyl myristate and isopropyl palmitate. Isopropyl myristate is the most preferred hardening liquid according to the invention, being the most versatile in its uses.

Isopropyl myristate and isopropyl palmitate are both in use as dermatological excipients and are known to have a very low order of toxicity. E.g. attempts to establish an $LD_{50}$ of isopropyl myristate in mice failed when dosages equivalent to 100 ml/kg did not affect the animals. Therefore these compounds are considered fully biocompatible. Moreover, they are not inflammable, nor are they detrimental to the environment.

The invention is therefore characterized in that in the step of hardening the microcapsules the hardening liquid is an ethyl or isopropyl ester of a straight-chain fatty acid having 12-18 carbon atoms or a mixture thereof.

Preferably, the volume of the hardening liquid used according to the invention is between 5-25 times the total volume of solvent and non-solvent.

In order to prevent the formation of microcapsules of irregular shape, the temperature during the hardening process is preferably kept between 3°-25° C. More preferably the temperature is kept between 3°-10° C. when isopropyl myristate or isopropyl palmitate are used for hardening poly-DL-lactide-co-glycolide or poly-L-lactide, and between 18°-25° C. when poly-DL-lactide is to be hardened.

Optionally the microcapsules can be washed after the step of adding the hardening liquid.

It will be appreciated that in principle all kinds of hydrophilic and lipophilic bioactive substances can be encapsulated in microcapsules according to the invention, especially when prolonged action is desired. Examples of hydrophilic bioactive substances are hormones and hormone-releasing factors and medicaments with anti-inflammatory, anti-peptic ulcer, anti-tumorous, anti-depressive, anti-hypertensive or antibiotic action. In particular peptides and proteins are suitable to be used as the hydrophilic bioactive compounds, such as adrenocorticotrophic hormones, angiotensins, blood clotting factors (factor VII, factor VIII), calcitonins, corticotrophin releasing factors, cellular growth-regulating factors (EGF, TGF-$\alpha$ and -$\beta$), endorphins, enkephalins, gastric inhibitory peptides, gastrins, gastrin releasing peptides, growth hormones, hemopoietic factors (IL-3, IL-6, CSF's and EPO), insulins, interferons, oxytocin, parathyroid hormones, somatostatin and vasopressins, and pharmacologically active analogues and fragments thereof.

Examples of lipophilic bioactive substances which can be microencapsulated according to the invention are the steroids. In particular the invention is useful for encapsulating beclomethasone 17,21-dipropionate, intended for controlled-release oral preparations against disorders of the intestine.

Further specific examples of bioactive substances which can be microencapsulated according to the invention are 4- and 5-aminosalicylic acid and Colloidal Bismuth Subcitrate, sold under the trademark De-Nol and also known as tripotassium dicitrato bismuthate.

The invention also includes the microcapsules prepared according to the described process as well as preparations, such as pharmaceutical preparations, which contain these microcapsules in a suitable carrier. In particular the invention includes injectable pharmaceutical preparations, in which the microcapsules are dispersed in a suitable liquid carrier, and oral pharmaceutical preparations, in which the microcapsules are dispersed in a suitable carrier.

EXAMPLES

The invention is further illustrated by the following Examples, which illustrate the best mode currently contemplated for carrying out the invention, but which must not be construed as limiting the invention in any manner.

EXAMPLE 1

Encapsulation of BSA in aqueous solution, in poly-L-lactide 100 mg of BSA (Sigma, art No. A 7030), were dissolved in 0.8 ml water. This solution, was added to a 300 ml Erlenmeyer containing 100 ml of a 2% solution of poly-L-lactide (Boehringer Ingelheim, lot. No. EC 8707, mean mol weight 220,000, inh. visc. 1.82 dl/g, in $CHCl_3$ at 25° C.) in dichloromethane. After 2 minutes of stirring (1000 RPM), 60 ml of silicone oil (Wacker AK 1000), was added while stirring, after which stirring was continued for another 15 minutes (300 rpm). The content of the Erlenmeyer was then poured into 1800 ml of isopropyl myristate (Henkel) at 5° C., which was also stirred (850 rpm) during a further 90 minutes, after which the microcapsules were sieved out of the liquid, using a sequence of 100, 50 and 25 $\mu$m sieves. Finally, the microcapsules were washed and dried.

The collected microcapsules were freely flowable, and on microscopical inspection they were seen to be generally spherical in form and to contain droplets of about 1-10 $\mu$m, evenly dispersed over the spherules. The amounts of microcapsules collected over the three sieves were:

| Microcapsule size | amount collected |
|---|---|
| 25-50 $\mu$m | 223 mg |
| 50-100 $\mu$m | 354 mg |
| >100 $\mu$m | 780 mg |
| | 1357 mg |

The content of BSA in the microcapsules was determined according to M. M. Bradford (Analyt. Biochem. 72 1976 248-254) and found to be 2.40% w/w, corresponding to a total content of BSA in the harvested microcapsules of 33 mg. This is a yield of 33% in BSA.

EXAMPLE 2

Encapsulation of dry BSA, in poly-DL-lactide co-glycolide 100 ml of a 10% solution in dichloromethane of poly-DL-lactide co-glycolide 50:50 (Boehringer Ingelheim, lot. No. EC 8713, mean mol weight 91,000, inherent viscosity 0.7 dl/g, in $CHCl_3$ at 25° C.) was added to 800 mg of BSA (Sigma, art. No. A 7030, sieved fraction of 2-21 $\mu$m particle size) in a dry reaction vessel, stirred at 1200 rpm for 5 minutes. Subsequently, while stirring at 400 rpm, 50 ml of silicone oil (Wacker AK 2000) was added during 1 minute, after which stirring was continued for another 5 minutes at 200 rpm. The content of the reaction vessel was then poured into 2000 ml of isopropyl myristate (Henkel) at 5° C., which was also stirred (850 rpm) during a further 2 hours, after which the microcapsules were sieved out of the liquid using a 25 $\mu$m sieve. The microcapsules were then washed, sieved again using a sequence of 140 and 25 $\mu$m sieves and dried.

The collected microcapsules were freely flowable. On microscopic inspection they were seen to be indented spherules. Their size was between 25 and 140 μm and their total yield 8500 mg, which is about 85 %. The content of BSA in the microcapsules was determined according to M. M. Bradford and found to be 4.73% w/w, corresponding to a total content of BSA in the harvested microcapsules of 402 mg. This is a yield of 50.2% in BSA.

EXAMPLE 3

Encapsulation of dry BSA in poly-DL-lactide

Microcapsules were prepared using similar steps as in Example 2, with the following modifications:

The polymer was poly-DL-lactide (CCA-Biochem, lot. No. C059, mean mol weight 19,000) as a 10% solution in dichloromethane.

The non-solvent was Dow Corning silicone oil DC 200 fluid 200 Cst.

Isopropyl myristate was used in an amount of 2500 ml at 20° C.

The collected microcapsules were moderately sticky. They were spherical in form, and between 25 and 140 μm in size. Their total yield was 7900 mg, which is about 80%. The content of BSA in the microcapsules was determined according to M. M. Bradford and found to be 3.5% w/w, corresponding to a total content of BSA in the harvested microcapsules of 276 mg. This is a yield of 43.8% in BSA.

EXAMPLE 4

Encapsulation of dry BSA in poly-DL-lactide co-glycolide. Hardening liquid: ethyl laurate 32 ml of a 10% solution in dichloromethane of poly-DL-lactide co-glycolide 50:50 (Resomer RG 505 Boehringer Ingelheim, lot. No. EC8713, mean mol weight 91,000, inherent viscosity 0.7 dl/g, in $CHCl_3$ at 25° C.) was added to 150 mg of BSA (Sigma bovine serum albumin prod. No. A-7030, sieved fraction of 2-21 μm part. size) in a 100 ml dry glass-beaker. BSA was dispersed by stirring at 1000 rpm for 5 minutes at room temperature. Subsequently, while stirring at 400 rpm, 16 ml of polydimethylsiloxane (Dow Corning DC 360, medical grade, viscosity 2000 cS) was added during 2 minutes. The content of the beaker was then added to 500 ml ethyl laurate (zur synthese, Merck art. 805334), at 20° C., which was also stirred (400 rpm) during a further 16 hours, after which stirring was stopped. After sedimentation of the microcapsules the isopropyl laurate was decanted. Then a fresh amount of 250 ml ethanol was added and stirred for 16 hours at 400 rpm. After stopping stirring and decanting again, 250 ml ethanol was added and stirred at 400 rpm during ten minutes. After the last washing procedures with ethanol, microcapsules were collected above a 10 μm teflon membrane filter by filtrating the ethanol. The microcapsules were dried during 24 hours under continuous vacuum conditions.

The total yield of microcapsules was 3.02 grams The yield of 25-160 μM microcapsules was 2.86 grams which is about 85.4%. The content of BSA was determined according to M.M. Bradford and found to be 2.3 w/w, corresponding to a total content of BSA in the harvested microcapsules of 0.066 gram BSA. This is a yield of 44.0% in BSA.

EXAMPLE 5

Encapsulation of dry insulin in poly-DL-lactide co-glycolide

Hardening Liquid: isopropyl myristate 200 ml of a 10% solution in dichloromethane of poly-DL-lactide co-glycolide 50:50 (Resomer RG 505 Boehringer Ingelheim, lot. No. EC7813, mean mol weight 91,000, inherent viscosity 0.7 dl/g, in $CHCl_3$ at 25° C.) was added to 1 gram of insulin (Sigma bovine insulin prod. No. I-5500 lot. No. 38F-0827 15 μm crystalline particles) in a 300 ml dry glass-beaker. The insulin was dispersed by stirring at 1200 rpm for 5 minutes at room temperature. Subsequently, while stirring at 400 rpm, 100 ml of polydimethylsiloxane (Dow Corning DC 360, medical grade, viscosity 2000 cS) was added during 2 minutes. The content of the beaker was then added to 4000 ml isopropyl myristate (Henkel), at 20° C., which was also stirred (400 rpm) during a further 24 hours, after which stirring was stopped. After sedimentation of the microcapsules the isopropyl myristate was decanted. Then a fresh amount of 1000 ml isopropyl myristate was added and stirred for another 24 hours at 400 rpm. After stopping stirring and decanting again, 400 ml ethanol was added and stirred at 400 rpm during ten minutes. After decanting the ethanol, the washing procedure was repeated. After the last washing procedure with ethanol, microcapsules were collected above a 10 μm membrane filter by filtrating the ethanol. The microcapsules were dried during 24 hours under continuous vacuum conditions.

The total yield of microcapsules was 20 grams. The yield of 25-140 μm microcapsules was 19.5 grams which is about 93%. The content of insulin was determined according to M. M. Bradford and found to be 3.9% w/w, corresponding to a total content of insulin in the harvested microcapsules of 0.760 gram insulin, this is a yield of 76.1% in insulin.

EXAMPLE 6

Encapsulation of dry insulin in poly-DL-lactide co-glycolide

Hardening Liquid: ethyl myristate 100 ml of a 10% solution in dichloromethane of poly-DL-lactide co-glycolide 50:50 (Resomer RG 505 Boehringer Ingelheim, lot. No. EC8713, mean mol weight 91,000, inherent viscosity 0.7 dl/g, in $CHCl_3$ at 25° C.) was added to 500 mg of insulin (Sigma bovine insulin prod. No. I-5500 lot. No. 38F-0827 15 μm crystalline particles) in a 300 ml dry glass-beaker. The insulin was dispersed by stirring at 1000 rpm for 5 minutes at room temperature. Subsequently, while stirring at 400 rpm, 50 ml of polydimethylsiloxane (Dow Corning DC 360, medical grade, viscosity 2000 cS) was added during 2 minutes. The content of the beaker was then added to 1500 ml ethyl myristate (zur synthese, Merck art. 818970), at 20° C., which was also stirred (400 rpm) during a further 2 hours, after which stirring was stopped. After sedimentation of the microcapsules the ethyl myristate was decanted. Then a fresh amount of 500 ml ethyl myristate was added and stirred for another 24 hours at 400 rpm. After stopping stirring and decanting again, 400 ml ethanol was added and stirred at 400 rpm during ten minutes. After decanting the ethanol, the washing procedure was repeated twice. After the last washing procedure with ethanol, microcapsules were collected above a 10 μm teflon membrane filter by filtrating the ethanol. The microcapsules were dried during 24 hours under continuous vacuum conditions.

The total yield of microcapsules was 9.01 grams. The yield of 25-140 μm microcapsules was 8.41 grams which is about 80.0%.

The content of insulin was determined according to M. M. Bradford and found to be 3.5% w/w, corresponding to a total content of insulin in the harvested microcapsules of 0.294 gram insulin. This is a yield of 58.9% in insulin.

EXAMPLE 7

Encapsulation of dry insulin in poly-DL-lactide co-glycolide

Hardening liquid: ethyl oleate 100 ml of a 10% solution in dichloromethane of poly-DL-lactide co-glycolide 50:50 (Resomer RG 505 Boehringer Ingelhe lot. No. EC8713, mean mol weight 91,000, inherent viscosity 0.7 dl/g, in $CHCl_3$ at 25° C.) was added to 500 mg of insulin (Sigma bovine insulin prod. No. I-5500 lot. No. 38F-0827 15 μm crystalline particles) in a 300 ml dry glassbeaker. The insulin was dispersed by stirring at 1000 rpm for 5 minutes at room temperature. Subsequently, while stirring at 400 rpm, 50 ml of polydimethylsiloxane (Dow Corning DC 360, medical grade, viscosity 2000 cS) was added during 2 minutes. The content of the beaker was then added to 1500 ml ethyl oleate at 20° C., which was also stirred (400 rpm) during a further 2 hours, after which stirring was stopped. After sedimentation of the microcapsules the ethyl oleate was decanted. Then a fresh amount of 500 ml isopropyl myristate was added and stirred for another 24 hours at 400 rpm. After stopping stirring and decanting again, 400 ml ethanol was added and stirred at 400 rpm during ten minutes. After decanting the ethanol the washing procedure was repeated twice. After the last washing procedure with ethanol, microcapsules were collected above 10 μm teflon membrane filter by filtrating the ethanol. The microcapsules were dried during 24 hours under continuous vacuum conditions.

The total yield of microcapsules was 9.01 grams. The yield of 25-140 μm microcapsules was 8.2 grams which is about 78.0%.

The content of insulin was determined according to M. M. Bradford and found to be 3.5% w/w, corresponding to a total content of insulin in the harvested microcapsules of 0.287 gram insulin. This is a yield of 57.4% in insulin.

EXAMPLE 8

Encapsulation of dry insulin in poly-DL-lactide co-glycolide

Hardening liquid: isopropyl palmitate 100 ml of a 10% solution in dichloromethane of poly-DL-lactide co-glycolide 50:50 (Resomer RG 505 Boehringer Ingelheim, lot. No. EC8713, mean mol weight 91,000, inherent viscosity 0.7 dl/g, in $CHCl_3$ at 25° C.) was added to 500 mg of insulin (Sigma bovine insulin prod. No. I-5500 lot. No. 38F-0827 15 μm crystalline particles) in a 300 ml dry glassbeaker. The insulin was dispersed by stirring at 1000 rpm for 5 minutes at room temperature. Subsequently, while stirring at 400 rpm, 50 ml of polydimethylsiloxane (Dow Corning DC 360, medical grade, viscosity 2000 cS) was added during 2 minutes. The content of the beaker was then added to 1500 ml isopropyl palmitate (Henkel cospha products lot 727067), at 20° C., which was also stirred (400 rpm) during a further 16 hours, after which stirring was stopped. After sedimentation of the microcapsules the isopropyl palmitate was decanted. Then a fresh amount of 500 ml isopropyl myristate was added and stirred for 10 minutes at 400 rpm. After stopping stirring and decanting again, 400 ml ethanol was added and stirred at 400 rpm during ten minutes. After decanting the ethanol the washing procedure was repeated twice. After the last washing procedure with ethanol, microcapsules were collected above 10 μm teflon membrane filter by filtrating the ethanol. The microcapsules were dried during 24 hours under continuous vacuum conditions.

The total yield of microcapsules wa 9.81 grams. The yield of 25-140 μm microcapsules was 3.10 grams which is about 30%.

The content of insulin was determined according to M. M. Bradford and found to be 3.4% w/w, corresponding to a total content of insulin in the harvested microcapsules of 0.105 gram insulin. This is a yield of 21.1% in insulin.

EXAMPLE 9

Encapsulation of beclomethasone 17,21-dipropionate in EUDRAGIT-RL. Hardening Liquid: isopropyl myristate 30 ml of a 10% solution in dichloromethane of EUDRAGIT-RL-100 was added to 0.333 g of beclomethasone 17,21-dipropionate in a 100 ml glass-beaker. The beclomethasone diproprionate was dissolved by stirring at 250 rpm at room temperature. Subsequently, while stirring at 250 rpm, 30 ml of polydimethylsiloxane (Wacker AK-1000, viscosity 1000 cS) was added during 1 minute. The content of the beaker was then added to 500 ml isopropyl myristate (Henkel), at 20° C., which was also stirred at 250 rpm during a further 24 hours, after which stirring was stopped. After sedimentation of the microcapsules the isopropyl myristate was decanted. The microcapsules were washed twice with 200 ml of N-hexane and collected above a 10 μm membrane filter. The microcapsules were then dried during 24 hours at room temperature.

The total yield of microcapsules was 3 grams, which is about 90%. The content of the beclomethasone 17,21-dipropionate as determined by HPLC was 7.9% w/w, corresponding to a total content of beclomethasone 17,21-dipropionate in the harvested microcapsules of 0.24 g, which is a yield of 72% w/w.

EXAMPLE 10

Residual content of different hardening liquids in mirocapsules

The residual content of isopropyl myristate in the microcapsules, prepared according to Example 2, was determined by Thin Layer chromatography and found to be 5% w/w.

The residual content of heptane in microcapsules, prepared according to Example 2 (isopropyl myristate replaced by heptane) was determined by Gas Liquid chromatography and found to be approximately 8% w/w.

The residual contents of Freon 113 and Freon 11 in microcapsules, prepared according to Example 2 of GB 2165517, were determined by gas-liquid chromatography and found to be 24% w/w and 19% w/w, respectively.

EXAMPLE 11

Release of BSA from microcapsules

Figure 1:
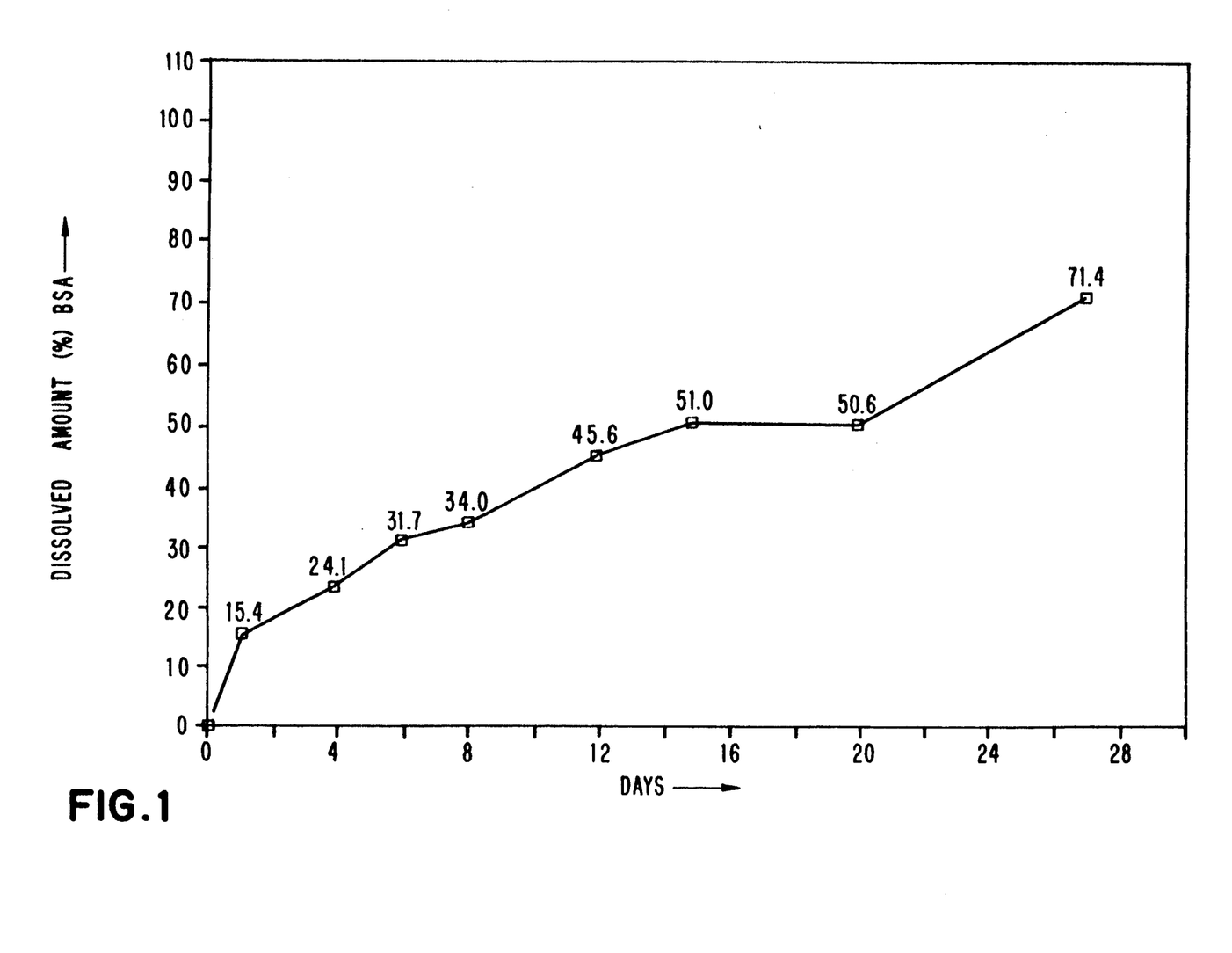
FIG. 1 is a graphic representation of the % release over time of bovine serum albumin (BSA) from microcapsules of the invention.

Ten samples of 50 mg of microcapsules, prepared according to Example 2, were placed each in 100 ml of phosphate buffer, pH 7.4, to which was added 100 mg of sodium azide. The vessels were kept during their follow-up periods at 37° C. and shaken at a rate of 37.5 cycles per minute. At different time intervals upto 28 days the complete microcapsules-content from one vessel was analysed for its residual BSA content, using the method of M. M. Bradford. The reciprocal results (dissolved BSA) are presented in figure 1 and show an approximately linear release of BSA upto 70% at 28 days.

EXAMPLE 12

Release of insulin from microcapsules

Figure 2:
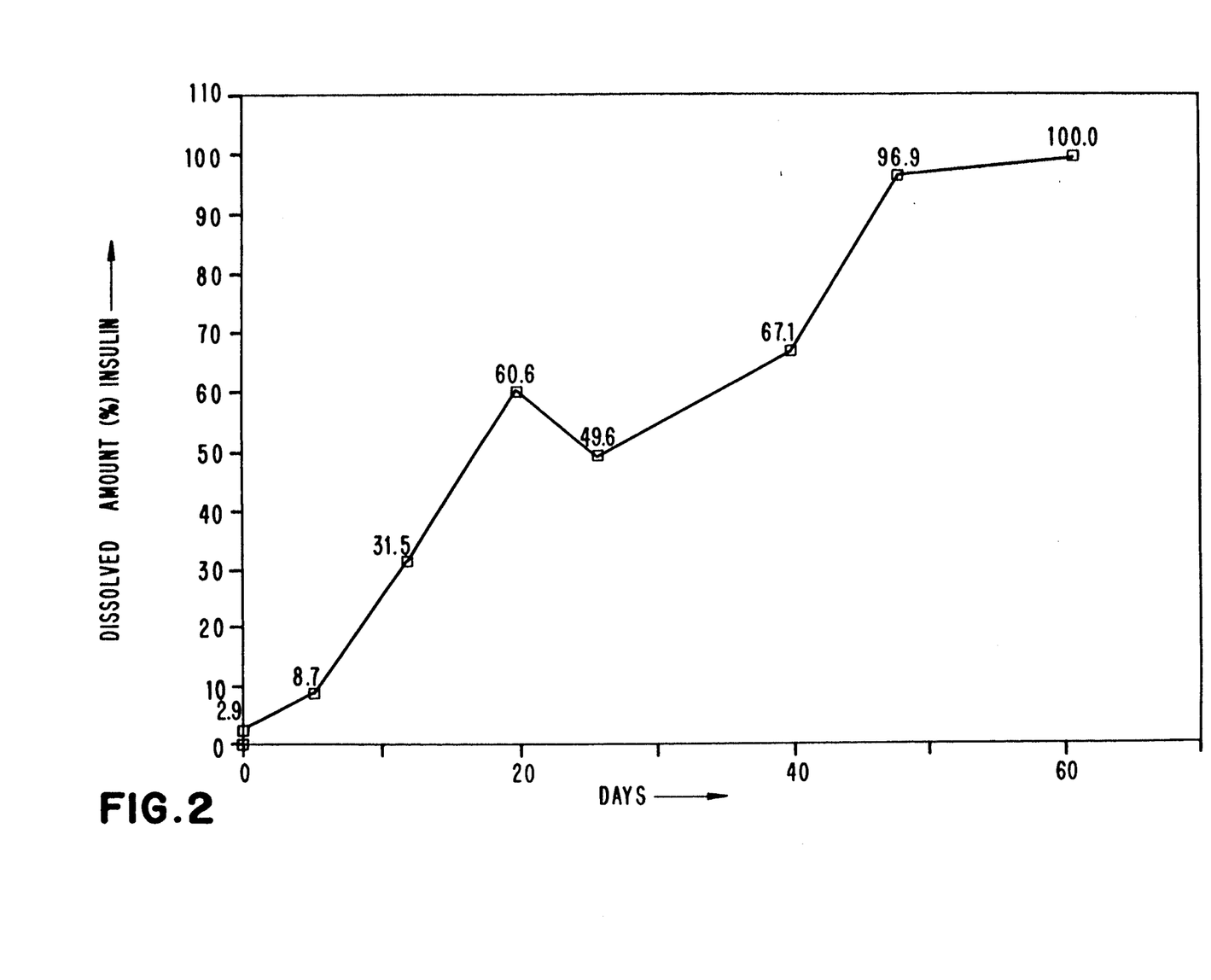
FIG. 2 is a graphic representation of the % release over time of insulin from microcapsules of the invention.

Nine samples of 60 mg of microcapsules, prepared according to Example 5, were placed each in 100 ml of phosphate buffer, pH 7.4, to which were added 372 mg of sodium EDTA and 100 mg of sodium azide. The vessels were kept during their follow-up periods at 37° C. and shaken at a rate of 37.5 cycles per minute. At different time-intervals upto 60 days the complete microcapsules-content from one vessel was analysed for its residual insulin content, using the method of M.M. Bradford. The reciprocal results (dissolved insulin) are presented in FIG. 2 and show an approximately linear release of insulin upto almost 100% at 50 days.

EXAMPLE 13

Figure 3:
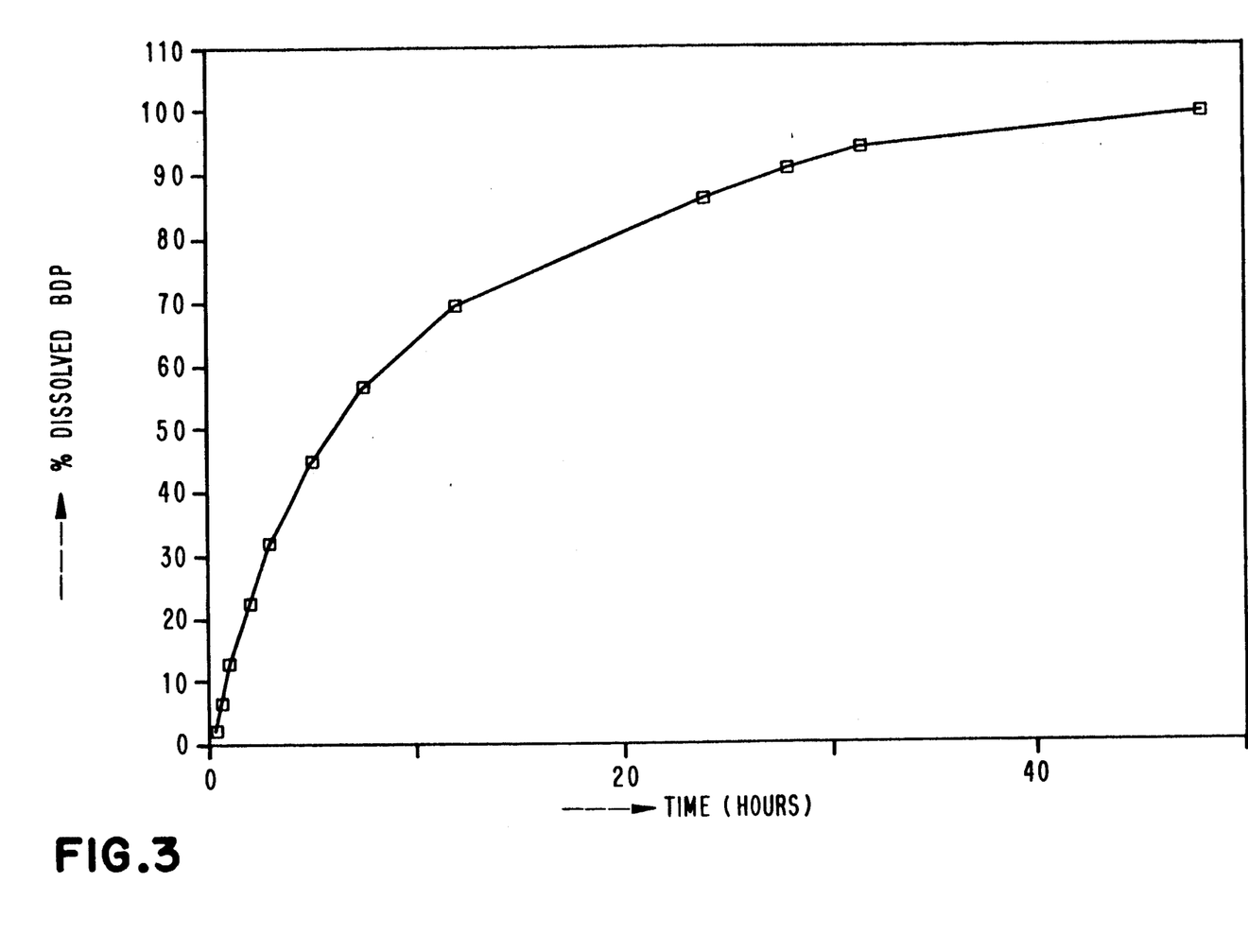
FIG. 3 is a graphic representation of the % release over time of beclomethasone 17,21-dipropionate from microcapsules of the invention.

Release of beclomethasone 17,21-dipropionate from microcapsules 40 mg of microcapsules, prepared according to Example 9, were placed in 500 ml of phosphate buffer, pH 7, to which was added 1% of CETOMACROGOL 1000. The USP-paddle dissolution system was used with a stirring speed of 100 rpm. The temperature was 37.C. At time intervals upto 48 hours a 1.5 ml sample was taken and filtered, and its beclomethasone 17,21-dipropionate content determined by HPLC against a standard of 6 µg/ml of beclomethasone 17,21-dipropionate in phosphate buffer of pH 7, containing 2% of CETOMACROGOL 1000. The mean results of 3 determinations, as shown in FIG. 3, clearly demonstrate a sustained release.

EXAMPLE 14

Encapsulation of 5-amino-salicylic acid in EUDRAGIT-RS

Hardening liquid: isopropyl myristate 100 ml of a 6% solution in dichloromethane of EUDRAGIT-RS-100 was added to 20 g of 5-amino-salicylic acid in a 300 ml vessel. The 5-amino-salicylic acid was suspended by stirring at 250 rpm at room temperature. Subsequently, while stirring at 250 rpm, 100 ml of polydimethylsiloxane (Dow Corning DC 360, viscosity 1000 cS) was added during 1 minute. After sedimentation of the microcapsules in-situ the liquid was decanted. The residual content of the vessel was then added to 800 ml isopropyl myristate (Henkel), at 20° C., which was stirred at 500 rpm during a further 24 hours, after which stirring was stopped. After sedimentation of the microcapsules the isopropyl myristate was decanted. The hardened microcapsules were washed twice with 200 ml of N-heptane and collected above a 10 µm membrane filter. The microcapsules were then dried during 24 hours at room temperature.

The total yield of microcapsules was 20 grams, which is about 77%.

EXAMPLE 15

Encapsulation of Colloidal Bismuth Subcitrate in ethylcellulose. Hardening liquid: isopropyl myristate The same procedure as described in Example 14 was carried out by using 20 g of Colloidal Bismuth Subcitrate as the biologically active substance, ethylcellulose N22 as the non-biodegradable polymer, and polydimethylsiloxane (Dow Corning DC360, viscosity 2000 cS) as the coacervation agent.

The total yield of microcapsules was 21.6 grams, which is about 83%.

EXAMPLE 16

Release of 5-amino-salicylic acid from microcapsules 340 mg of microcapsules, prepared according to Example 14, were placed in 1000 ml of phosphate buffer, pH 7.5, to which was added 0.1% PLURONIC F-68.

The USP-paddle dissolution system was used with a stirring speed of 100 rpm. The temperature was 37° C.

At time intervals upto 12 hours the absorbance at 326 nm was measured using a spectrophotometer equiped with a continuous-flow sampling system.

The 5-amino-salicylic acid content was calculated using the absorbance value of a standard of 260 µg/ml of 5-amino-salicylic acid in phosphate buffer of pH 7.5, containing 0.1% PLURONIC F-68.

Figure 4:
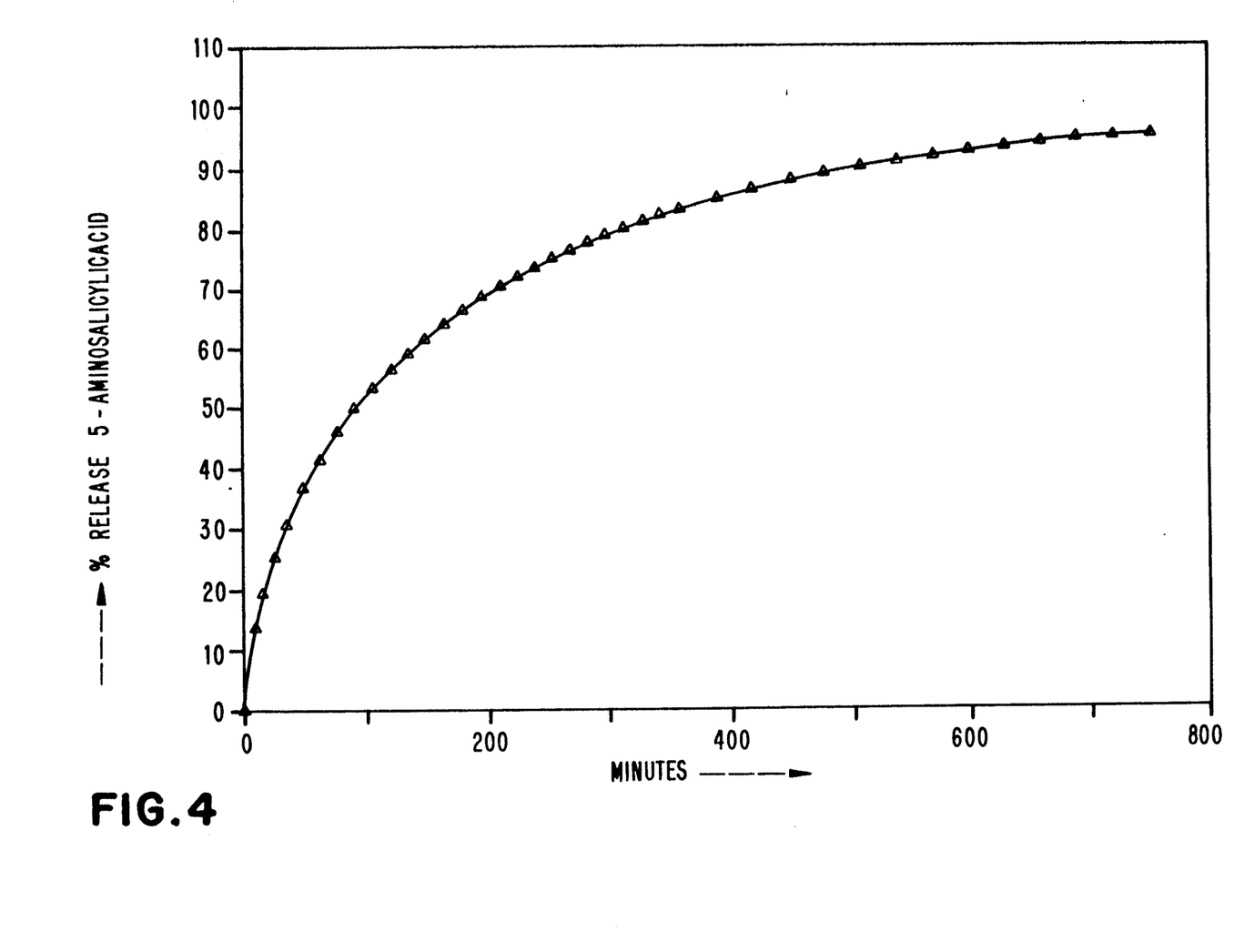
FIG. 4 is a graphic representation of the % release over time of 5-aminosalicylic acid from microcapsules of the invention.

The results, as shown in FIG. 4, clearly demonstrate a sustained release.

We claim:

1. A process for microencapsulating bioactive compositions according to the phase separation principle, whereby microcapsules are formed by:
    a. dispersing the bioactive composition in an organic solution of a biocompatible polymer;
    b. adding a coacervation agent to the dispersion;
    c. adding a hardening liquid to the dispersion and
    d. collecting, washing and drying the resultant microcapsules, the improvement comprising adding as the hardening liquid an ethyl or isopropyl ester of a straight chain fatty acid having 12–18 carbon atoms to the dispersion in an excess with respect to the combined volume of solvent and coacervation agent.

2. The process according to claim 1, in which the hardening liquid is isopropyl myristate or isopropyl palmitate.

3. The process according to claim 1, in which the volume of hardening liquid added is 5–25 times the combined volume of solvent and coacervation agent.

4. The process according to claim 1, in which the bioactive composition is a hydrophilic composition.

5. The process according to claim 4, in which the hydrophilic composition is a protein.

6. The process according to claim 4, in which the hydrophilic composition is a peptide or protein selected from the group consisting of adrenocorticotrophic hormone, angiotensin, blood clotting factor, calcitonin, corticotrophin releasing factor, cellular growth regulating factor, endorphin, enkephalin, gastric inhibitory peptide, gastrin, gastrin releasing peptide, hemopoietic factor, growth hormone, insulin, interferon, oxytoxin, parathyroid hormone, somatostatin and vasopressin and pharmacologically active analogues and fragments thereof.

7. The process according to claim 4, in which the hydrophilic composition is Colloidal Bismuth Subcitrate.

8. The process according to claim 4, in which the hydrophilic composition is 4-aminosalicylic acid or 5-aminosalicylic acid.

9. The process according to claim 1, in which the bioactive composition is a lipophilic composition.

10. The process according to claim 9, in which the lipophilic composition is a steroid.

11. The process according to claim 9, in which the lipophilic composition is beclomethasone 17,21-dipropionate.

12. The process according to claim 1, in which the biocompatible polymer is biodegradable.

13. The process according to claim 1, in which the biocompatible polymer is a biodegradable polymer selected from the group consisting of poly-L-lactide, poly D,L-lactide or a copolymer of D,L-lactide and glycolide.

14. The process according to claim 1, in which the biocompatible polymer is non-biodegradable.

15. The process according to claim 1, in which the biocompatible polymer is a non-biodegradable polymer selected from the group consisting of ethylcellulose, EUDRAGIT-RL, EUDRAGIT-RS, EUDRAGIT-NE, EUDRAGIT-L, EUDRAGIT-S, hydroxypropyl methylcellulose phthalate, cellulose acetate phthalate, cellulose acetate trimellitate, propylvinyl acetate phthalate or shellac.

16. Microcapsules prepared according to claim 1.

17. A pharmaceutical preparation comprising microcapsules prepared according to claim 1 dispersed in a pharmaceutically acceptable carrier.

18. An injectable pharmaceutical preparation comprising microcapsules prepared according to claims 1 dispersed in a pharmaceutically acceptable liquid carrier.

19. An oral pharmaceutical preparation comprising microcapsules prepared according to claim 1 dispersed in a pharmaceutically acceptable carrier.

* * * * *